United States Patent [19]

Dechene et al.

[11] Patent Number: 5,396,806
[45] Date of Patent: Mar. 14, 1995

[54] ON-LINE MASS FLOW MEASUREMENT IN FLOWING TWO COMPONENT SYSTEMS

[75] Inventors: Ronald L. Dechene; David R. Day, both of Boxford, Mass.; Thomas B. Smith, Atkinson, N.H.

[73] Assignee: Auburn International, Inc., Danvers, Mass.

[21] Appl. No.: 150,961

[22] Filed: Nov. 12, 1993

[51] Int. Cl.$^6$ .............................................. G01F 1/74
[52] U.S. Cl. .................................................. 73/861.04
[58] Field of Search ............... 73/861.04, 61.71, 53.04; 324/434

[56] References Cited

U.S. PATENT DOCUMENTS

| | | | |
|---|---|---|---|
| 3,006,189 | 10/1961 | Warren et al. | 73/861.04 |
| 3,635,082 | 1/1972 | Prellwitz et al. | 73/861.04 |
| 4,063,153 | 12/1977 | Dechene et al. | 324/434 |
| 4,074,184 | 2/1978 | Dechene et al. | 324/434 |
| 5,095,758 | 3/1992 | Cox et al. | 73/861.04 |
| 5,259,239 | 11/1993 | Gaisford | 73/861.04 |

Primary Examiner—Richard E. Chilcot, Jr.
Assistant Examiner—Harshad Patel
Attorney, Agent, or Firm—Jerry Cohen; Edwin H. Paul

[57] ABSTRACT

Apparatus and process for measuring mass flow of a slurry mixture of two components of materials, such as a flow of catalyst solid particles (the first component) or droplets in a fluid carrier (the second component). The slurry mixture is added to a process stream (10) or batch reactor. The flow velocity and the volume fraction of one component are measured and combined with the known specific gravity, of the component being measured, and the physical dimensions of the pipe, in which the slurry mixture is flowing, to determine the mass flow of the component. The flow velocity is measured by correlating signals at two separated locations along the flow path, and the volume fraction is measured by combining the known dielectric constants of each of the materials in the mixture and the measured capacitance of the mixture. The capacitance is measured from electrodes which may be isolated from the flowing materials in some applications, but not isolated from the flowing materials in other applications. The temperature (9) and pressure (11) are compensated in the final calculation, and the mass flow result is used to control, via feedback, the amount of such materials delivered. Also, a subtraction technique to remove interfering power line noise is implemented to improve sensitivity.

7 Claims, 5 Drawing Sheets

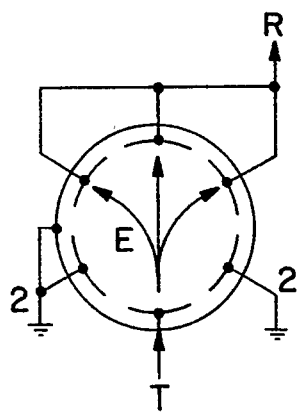 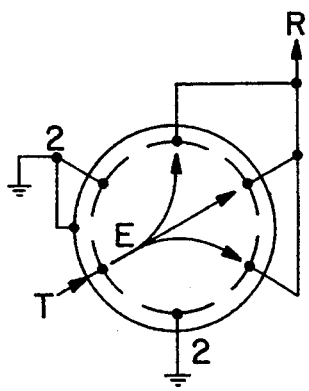 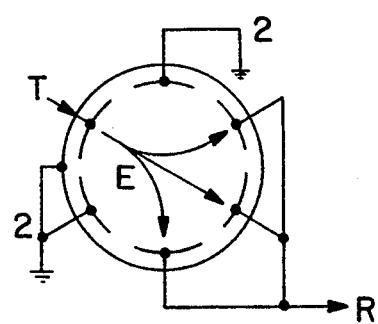
FIG. 2A   FIG. 2B   FIG. 2C
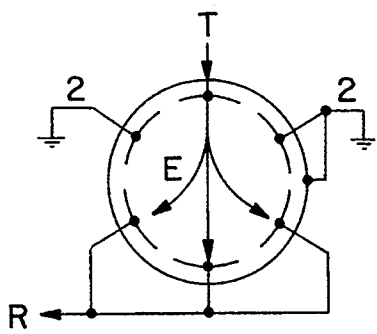 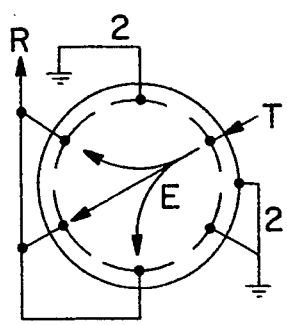 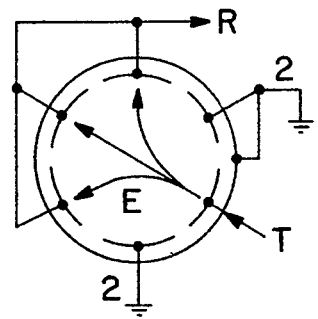
FIG. 2D   FIG. 2E   FIG. 2F

ON-LINE MASS FLOW MEASUREMENT IN FLOWING TWO COMPONENT SYSTEMS

CROSS REFERENCE TO RELATED APPLICATIONS

This application is closely related to U.S. Pat. Nos. 4,074,184 ('184), issued Feb. 14, 1978, entitled "Nonconductive Vapor/Solid or Liquid fraction Determination, and 4,774,453 ('453), issued Sep. 27, 1988, entitled "Measuring Flow of Insulating Fluids". These patents are of common assignment with this application, and their disclosures are hereby incorporated herein by reference, as though set out at length herein.

FIELD OF THE INVENTION

The present invention relates to mass flow rate measurements in two component systems and more particularly to mass flow rate measurement of solid particles in a liquid hydrocarbon carrier. The present invention relates to such two component flowing systems, in some instances where the components are miscible and immiscible, and where the materials are conductive or nonconductive. Even more particularly the present invention relates, but not exclusively, to accurate monitoring and precise controlling of catalyst introduction into polyolefin processes.

BACKGROUND OF THE INVENTION

Mass flow measurement systems have used off-line techniques where the flow is accumulated over time, the fractions separated out and then weighed. Such techniques are slow and may not represent the actual conditions of real-time on-line feed systems. Herein mass flow and mass flow rate are used interchangeably.

Measurement of mass flow rate is relatively direct for one component systems. Herein "component" is defined as a gaseous, liquid or solid state of material. But, for mass flow rate measurement in multi-component systems, the fundamental problem is separating out the mass flow of a single desired component when the relative proportions of the multi-component mixture vary. This problem must be solved in a commercially effective technique.

As disclosed in the '453 patent, the velocity or flow rate of a slurry is measured by correlating a detectable signature of the flowing material upstream and downstream and with the time elased between the corralated signatures the velocity of flow can be determined. However, if the pattern changes between the two sensors, the correlation may be degraded and errors may occur. For thsi reason, the '453 patent places the sensor electrodes close to each other.

As discussed in the '184 patent, the volume fraction of each cmponent is measured indirectly where six electrodes, arranged around the flow pipe, are used to measure capacitance with the flowing components providing the dielectric material. The technique uses the fact that the different components each have different dielectric constants that affect the measured capacitance. But, a difficulty occurs due to the non-uniformity of th electric field distribution when the sensors are hemicylindrical, or part of cylinders. The '184 patent uses six circumferential electrodes placed around the insulated pipe section. The capacitance between a first electrode and the three opposing electrodes in measured; then the measurement is made between the electrode next to the first and the corresponding three opposing electrodes. This rotating measurement process is repeated until six measurements (covering all six electrodes) are made at high speed. The high speed is necessary to measure the capacitance of the contents of the pipe while only negligible flow occurs. One continuing limitation of prior art systems is that, although the electric field is rotated, there are still several zones of lower sensitivity within a cross section of the pipe. If, in a two component system, the components are non-uniformly distributed across high and low sensitivity zones, then some inaccuracy in the measured value may occur.

A limitation in mass flow measurement systems is the power line generated noise that reduces sensitivity in such systems.

Another limitation of such systems that utilize capacitive measurements is that the dielectric constants of the slurry materials will change with temperature and with pressure.

Accordingly it is an object of the present invention to incorporate correction factors for temperature and pressure into such volume fraction measurements.

It is an object of this invention to provide an improved electrode design to overcome the above illustrated limitation.

Another object of the present invention is to recognize power line generated noise and by manipulating the data substantially eliminate such noise from the stored signal data.

It is another object of the present invention to provide rapid on-line mass flow measurements suitable for use as a feedback or feedforward control parameter for controlling a processing system.

The above incorporated patents were advanced in the art for determining the volume fraction of the solid in a slurry ('184) and a solid-liquid slurry velocity ('453). An important object of the present invention, is to combine these two measured parameters with the known density of the catalyst to yield the mass per unit time or mass flow, in order to reduce waste while improving quailty of the resulting polyolefin product.

SUMMARY OF THE INVENTION

The foregoing objects are met in an on-line system with calculation capability to provide real time mass flow rates of two component slurries (particularly, in a preferred embodiment, with low volume fractions of solids, such as catalyst particles of high surface area or like materials, in a fluid carrier) useful in determining and controlling the total mass of catalyst delivered to a subject process. Tha apparatus includes knowing the cross section area of the pipe and the specific gravity of the fraction for which measurement and/or control is desired. The volume fraction of each component is measured, the velocity of the flow is measured, whereupon the volume and velocity parameters are input to a computer (herein defined as any processor, controller or computer system including, but not limited to, mini, personal, distributed, and micro computers or microprocessors configured as computers) which determines the mass flow for at least one of the components by multiplying together the volume (fraction) of that component, that component's specific gravity, the cross section area and the flow velocity. If specific gravity is not known, the volume flow rate can still be measured and is a useful parameter. Of course, parts or all of the foregoing could be accomplished with analog circuitry or other special purpose hardware and/or software.

The objects are met in a system for measuring on-line mass flow, in a two-component mixture of materials where, at least, one component is of known specific gravity, and where the materials are flowing in a pipe of conduit of known cross section area. This process includes: apparatus for sequentially measuring the capacitance between a plurality of electrodes, said electrodes dispersed circumferentially to the flow such that the electric field lines in such capacitances, when charged, are about normal to the flow direction and where the field lines penetrate the flow, and averaging the capacitance measurements such that the effects of non-uniformities of the flow patterns are reduced (through electric field rotation as the different circumferentially spaced electrodes are used in the measurements). Next, the averaged capacitance value is related to the dielectric constant of each flow component or to previously calibrated capacitances, from which the volume fraction is established. The flow velocity is measured, and the mass flow is determined by multiplying the following together: the volume fraction, the velocity, the specific gravity of the fraction material being measured, and the cross section area. In this process, in a preferred embodiment, the measuring of the volume fraction includes use of an extended form of the electrodes in a spiral generally along the axis of flow, the spiral having a pitch and a length such that irregular distributions of the components in the flow pattern and in the electric field(s) are compensated.

In a preferred embodiment, temperature and pressure sensors in the slurry flow provide correction factors that are incorporated into the mass flow determination, and in another preferred embodiment a desired mass flow of at least one component is determined and the difference between the measured mass flow and the desired mass flow is used as an error signal in a feedback system so that the measured mass flow about equals the desired mass flow.

In another preferred embodiment, the electrodes of the component volume measurement apparatus are designed in a spiral or double counter spiral fashion generally along the axis of flow to cancel out flow distribution inconsistencies.

Other objects, features and advantages will be apparent from the following detailed description of preferred embodiments thereof taken in conjunction with the accompanying drawings in which:

BRIEF DESCRIPTION OF THE DRAWINGS

FIGS. 2A–2F are pictorial sketches of the electric field distribution inside the pipe and the electric field distribution as the various electrodes are activated for the capacitance measurement;

DETAILED DESCRIPTION OF PREFERRED EMBODIMENT

PRINCIPLES OF OPERATION

A. Volume Fraction Measurement

Figure 1:
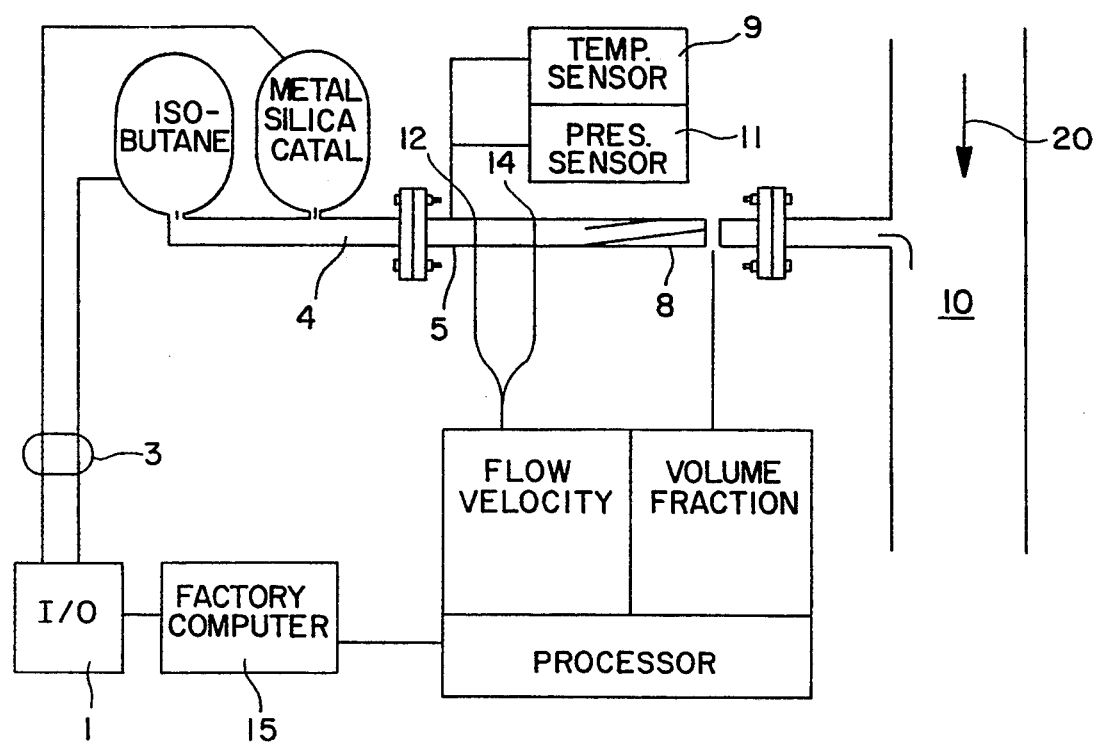
FIG. 1 is a schematic block diagram of a preferred embodiment of the invention.

Mass flow measurement of one component, in a two component phase slurry, in accordance with the present invention, is a technique based on the fact that each component of a two component system will generally have a different dielectric constant. There are, at least, two techniques for measuring volume fraction based on this fact.

One approach is to develop a calibration chart or curve of capacitance measurements against volume fraction, as follows: plot the average of the capacitance measurements (using the multiple radial electrodes in a fashion which rotates the electric fields, as described above) with only one component flowing in the pipe, then repeat and plot such measurements with a known volume of the second component (together with the first component) flowing in the pipe. The amount of the second component is preferably in the volume range expected. Volume fractions may then be determined from measured capacitances by drawing a line between the two calibration points, by linear interpolation, or like technique. In another preferred embodiment, the measurements are taken with the proportions of the second component varied from zero to 100% in steps as fine as necessary to achieve the desired accuracy (0.1% to 50%, in preferred embodiments). Other techniques utilize non-uniform step sizes. In such a fashion the calibration chart of capacitance measured versus volume fraction is developed. When an unknown volume fraction must be determined, the capacitance is measured and the value placed on the calibration chart from which the volume fraction is directly read.

Another approach is based on the fact that in a two component mixture the dielectric constant of the mixture will be somewhere between the dielectric constants of each component. The relationship between the dielectric constant of each phase and the measured dielectric constant of the mixture is modeled as a series-like combination of capacitances according to Eq. 1, as follows:

$$E_o = (f_a/E_a + f_b/E_b)^{-1} \qquad \text{Eq. 1}$$

where $E_o$ is the dielectric constant for the mixture, $E_a$ the dielectric constant of component a, $E_b$ the dielectric constant of component b, $f_a$ the volume fraction of component a, and $f_b$ the volume fraction of component b. Here $f_a + f_b = 1$; since the two components comprise the entire volume. If $f_a = 1 - f_b$ is substituted into Eq. 1, we have Eq. 2, as follows:

$$f_b = (1/E_o - 1/E_a)(1/E_b - 1/E_a)^{-1}, \qquad \text{Eq. 2}$$

thus the volume fraction of either of the two components can be found by knowing the dielectric constant of the mixture and of each component.

In some preferred embodiments the capacitance model may be a parallel arrangement (where the dielectic constants add) or a complex arrangement of series and parallel capacitances. In such cases a calibration curve is developed and the model fitted to the calibration curve or the equation of the calibration curve is derived by known techniques and such an equation is used in place of the calibration chart.

Such systems are influenced in practice by stray capacitance which are always present. When a calibration curve is developed the stray capacitance appears as a constant offset which usually will not affect the measurement. However, when a capacitance ratio is used, the stray capacitance will always present an error: hence the calibration curve approach is the preferred choice in many cases.

When a conductive component is used (as a non-continuous phase), the above techniques will still apply in cases where the impedance across the entire flow stream is dominated by the impedance of the insulating phase (the capacitance of the insulating phase). That is, the conductive component does not significantly contribute to the overall impedance of the component flow. Here, without considering stray capacitance, the volume fraction of the conductive component can be determined by measuring the capacitance (referenced as Co, below), as above detailed, without the conductive component and with the conductive component (reference as Ca, below). The increased capacitance is directly related to the volume of the conductive component, as illustrated by the following equation:

$$f_b = 1 - (C_a/C_o) = 1 - (E_a/E_o), \qquad \text{Eq. 3}$$

as shown, the volume fraction of the conductive part can be expressed in terms of the ratio between the capacitances or (in effect) the dielectric constants (again without including stray capacitance).

The volume fraction is compensated for temperature and for pressure by incorporating such correction factors into Eq. 2. The dependencies of these parameters are determined off-line for the materials of interest and such dependencies directly affect the dielectric constants which are then used in Eq. 2 by substituting for each E a corrected value of E(Ktemp) (Kpres), where these K's are found in the literature (such K's are not hereby defined as only linear multipliers), or, alternatively, such correction factors may be measured and applied to dielectric constants or measured capacitances.

C. Velocity of Flow Measurement

The velocity of flow is measured by correlating small random, or forced, charge accumulations in/on the flowing material. Frictional triboelectric phenomena generate static charges which can be detected upstream and subsequently downstream whereby the time between such detection is measured, and from which the velocity can be determined, as described below. In practice this charge build up can later cause a bothersome discharge, and, so to prevent any such discharge, the charge must often be shunted to a ground somewhere in the system.

A preferred embodiment utilizes a section of electrically insulating pipe that permits static charge to accumulate and persist over a distance from before-to-after the following described two rings. There are two conductive ring electrodes that are distributed around the flow at a distance from each other along the axis of the electrical insulating pipe, but with the rings electrically insulated from the flow by the pipe. The rings are distributed on the outside of the pipe in this preferred embodiment. But, in another preferred embodiment, the rings are coated with an electrical insulator and positioned on the inner surface of the pipe. As charges pass through the rings, a charge is capacitively induced in the electrical conductor connected to each ring, and this charge is subsequently converted to a voltage via suitable electronics. This voltage is amplified and digitized (via analog/digital converters) and stored in a memory. The digitized waveforms from each ring are then correlated as shown below by known mathmatics. The time difference between the receipt of such waveforms at each ring, together with the known ring, to ring distance allows a direct calculation of the velocity of flow.

The correlation of the waveforms via cross correlation techniques is well known in the field and can be expressed in Eq. 3, as follows, for two digitized signals A and B:

$$CC(s) = 1/n * \Sigma\, A(i) * B(i+s), \qquad \text{Eq. 3}$$

where $\Sigma$ is summed from $i=1$ to $i=n$, where n is less than the number of data points (m) stored for the digitized signal from either electrode.

Figure 3:
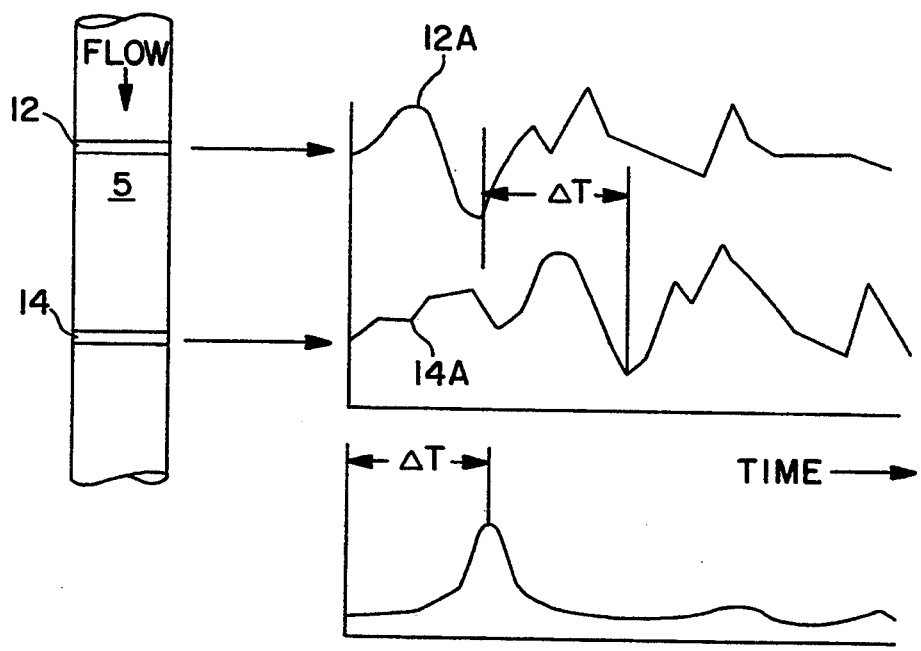
FIG. 3 is a pictorial sketch and graph associated with measuring velocity of flow.

Here, CC(s) is the calculated correlation coefficient associated with the integer interval s, where $n+s<m$. These limits ensure that the operations use only the data points available. The operation in lay terms is best described as follows: the correlation involves taking a portion of the upstream waveform data points and multiplying those points by the corresponding data points of the downstream waveform and summing the products; and then repeating this process but with each repetition shifting the relative positions of the two sets of data points with respect to each other. Each shift represents a time shift. The resulting point by point multiplication, over the portions used, is summed and averaged and called the Correlation Coefficient (CC). As the shift increases, and if there is an incidence of the same or nearly the same signal appearing at both the upstream and downstream sensors, the shift will eventually cause the matching curves to overlay each other. At this point the correlation coefficient will be a maximum, and at this point the shift will exactly be the transit time of the material as it flows from the upstream sensor to the downstream sensor. If the separation between the two sensors is known then velocity of the flow is found directly by dividing the separation by the transit time. FIG. 3 diagrammatically demonstrates the maximum correlation coefficient occurring at the transit time of the flow between the sensors.

D. Mass Flow Determination

The mass flow, MF, of a component B can be calculated directly from the following Eq. 4, as follows:

$$MF = (b)(V)(A)(p), \qquad \text{Eq. 4}$$

where the fraction that B represents is (b); the flow velocity is (V); the cross sectional area of the pipe is (A); and the specific gravity of the B component is (p).

PREFERRED EMBODIMENT STRUCTURES

FIG. 1 shows a system with ethylene flowing 20 in a pipe 10. Two components, iso-butane 7 and a metal silica catalyst 13, are mixed in a pipe 4 (with a flanged section 5) and then fed into the ethylene flow. The present invention, in this preferred embodiment, determines the mass flow of the catalyst.

FIG. 1 shows, in block diagram form, an entire preferred embodiment of the present invention, and FIG. 2 shows the distribution of six electrodes 8 distributed around the pressure pipe 4. The electrodes are around the inner side of the pressure pipe 4, but each electrode is isolated from the flow by a non-conductive liner 6. In other preferred embodiments the electrodes are not isolated from the flow. Each of the six electrodes is driven in sequence by an alternating electrical potential (AC) and the resulting current is sensed at the three opposing electrodes. The relationship of the driving potential and the resulting current depends substantially exclusively on the capacitance between the participating electrodes. This process continues at high speed making several hundred equivalent revolutions per second. The entire pipe volume is effectively averaged resulting in an accurate overall dielectric constant (Eo) measurement. The required speed is relative to the flow in the pipe, but, even with small micro-processors, such speed is high enough to effectively "freeze" the material flow while the fraction is measured. Referring to FIG. 1, the arrangement of the electrodes is in a spiral pattern distributed along the axis of the pipe cylinder. In this preferred embodiment the spiral makes a "left-hand" screw thread looking away from the ethylene flow process 10. In another preferred embodiment an opposite (in this case right-handed) distribution (not shown) can be made, and in yet other embodiments combinations of spiral directions and pitch of said spirals can be constructed. For example, a spiral may be a left-hand thread for a given distance, and then change to a right-hand thread.

Spirals, combinations of spirals, as described above, and like electrode configurations, are used to cancel out irregular distributions in the electric field and in the material flow pattern. Combinations of spirals are used specifically to cancel out those instances where spiral flow conditions are found.

In the preferred embodiment of FIG. 1, the pipe has a flanged segment 5 where the velocity and fraction sensors are located. This segment is round, about one inch internal diameter, and 12 inches long. In other preferred embodiments, the pipe may be of greater or less diameter with the length increased or decreased about proportionately. Since the flowing stream within the pipe segment 5 may be pressurized, this preferred embodiment is designed for 1000 psi (pounds per square inch) at 212° F. The sensor segment 5 may be designed for other pressures and temperatures as is well known in the art.

The block schematic diagram of FIG. 1 also shows the supporting electronics for implementing a working feedback system to control the mass flow of, at least, one component of a slurry mixture. A desired mass flow of one component is entered into the controller 15, with the physical constants of specific gravity and the temperature and pressure responses of both components, and the flow pipe physical dimensions. A temperature sensor 9 and a pressure sensor 11 monitor the temperature and pressure within the flow pipe 5 and send such signals to the controller so that the controller can provide a corrected mass flow determination. The velocity and volume fraction of the component are measured and input to the controller in which the mass flow calculation of that component is made. The controller determines the difference, between the desired mass flow and the measured mass flow, creating an error signal. Output signals 3 are fed via interface electronics 1 from the controller to the insulating liquid (isobutane) feeder 7 and catalyst feeder 13. In other preferred embodiments, other liquids and solid powders are used. The system is designed so that the controller, in response to the error signal, alters these feed rates to minimize the error signal by known methods. Such practical systems, in other preferred embodiments (not shown), are computer controlled where the mass flow is stored and displayed and where such data are compared to desired mass flow rates where the system is controlled via known feedback techniques (with such inherent transport lags) to provide for a controlled, settable mass flow.

FIG. 2 shows the electric field distribution between the electrodes as the measurements are taken around the circumference of the pipe. In this preferred embodiment, as each electrode is driven, indicated by T, the two adjacent electrodes 2 are grounded and the current is measured in the opposing three electrodes R. However, in other preferred embodiments, one or combinations of several electrodes are driven, and the corresponding current measured in one or combinations of several of the undriven electrodes. Also, in other preferred embodiments, the undriven electrodes where current is not measured may be grounded or left floating.

FIG. 3 shows the ring sensors for measuring flow velocity within the pipe 5. The upstream sensor 12 produces the signal shown 12A and the downstream sensor 14 produces the signal shown 14A. These signals 12A and 14A are drawings of actual curves that have been measured. Note that by visual inspection the curve 12A "correlates" closely in shape to the curve 14A. If the curve 12A is shifted horizontally by the amount $\Delta T$, the two curves 12A and 14A nearly match. As noted, if curve 12A is shifted by $\Delta T$, the point by point multiplication and summation of the two curves will produce a maximum correlation coefficient value.

Figure 4:
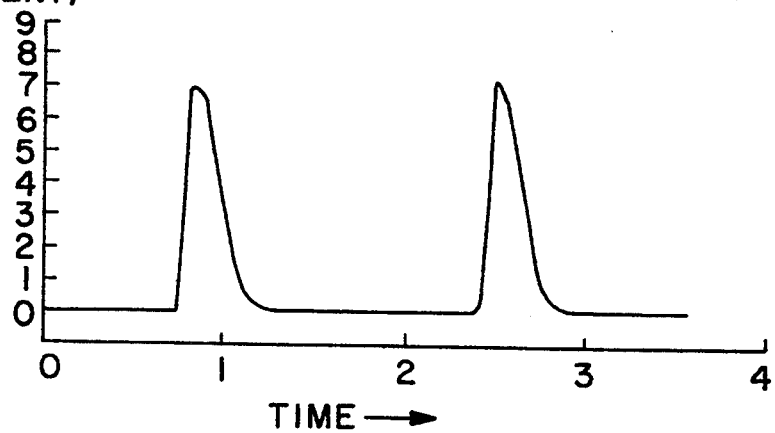
FIG. 4 is a graph of a trace catalyst feed vs. time realized in an example of a volume fraction determination in accordance with the invention.

FIG. 4 shows an example of data from a solid metallized silica catalyst in a liquid hydrocarbon carrier as a function of flow time. Initially there is only pure liquid. This is followed by a "pulse" of catalyst which slowly disperses as it is washed away into the process.

Figure 5:
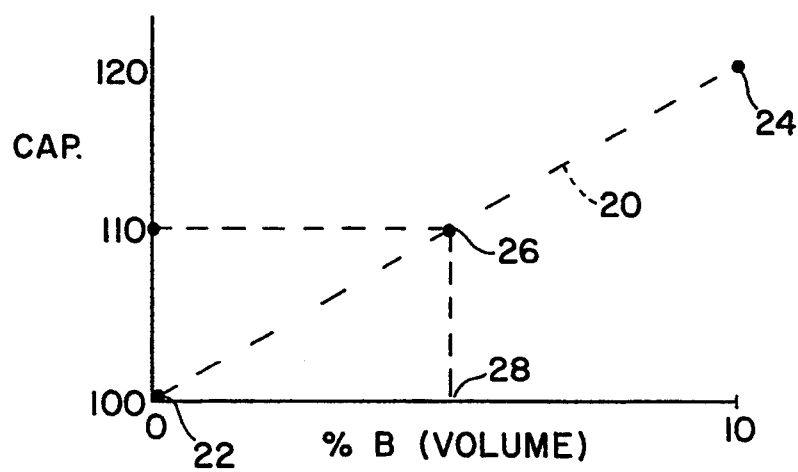
FIG. 5 is a graph of a calibration curve.

FIG. 5 is an example of a two point calibration curve 20 generated with a volume of zero percent of component B defining point 22. Point 22 represents a capacitance value (vertical scale) of 100. The second point is generated with volume of ten percent B defining point 24. The representative capacitance is 120. Note, the vertical scale is simply representative and does not relate to specific measurements. When an unknown mixture of the two components, represented in FIG. 5, is measured the capacitance value 110 is placed on the curve 26 and the volume percentage of 5 is read on the horizontal scale.

Figure 6:
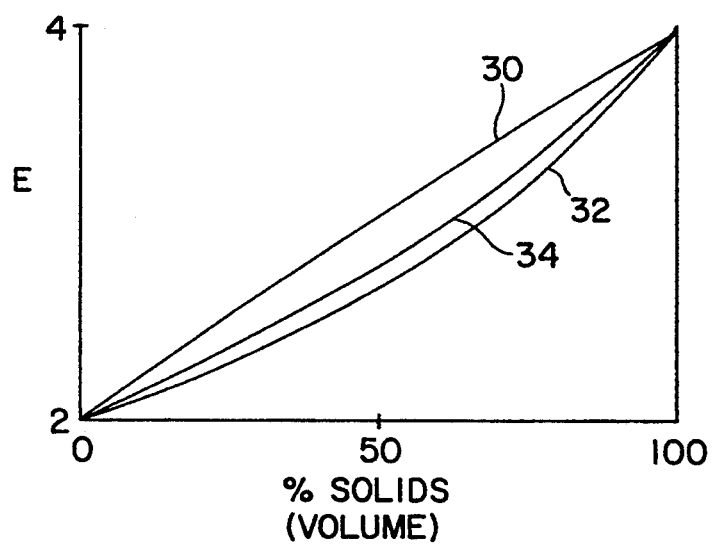
FIG. 6 is a graph of the dielectric constant of a two component slurry as generated from the equation models.

FIG. 6 shows a graph of different modelings of equations that represent a mixture of two components versus the dielectric constant E of the mixture. A parallel capacitance model is shown as curve 30, a series capacitance model as curve 32, and a computer generated finite difference simulation as curve 34. These curves are generated over a range of a solid phase component from 0% to 100%, where the solid component has a dielectric constant of 4 and the flowing continuous phase component has a dielectric constant of 2. The vertical scale values are representative of the dielectric constant of the mixture, but, also, are representative of the actual measured capacitance in a known physical system so no units are specified. A parallel model gives the straight line 30, the series model the curved line, and the computer simulation of an actual flow distribution gives a curved line 34 that is close to the series model.

Figure 7:
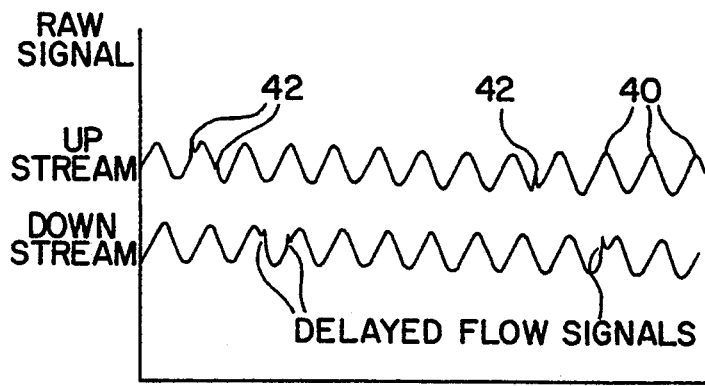
FIG. 7 is a graph of up and down stream flow data with a 60 Hz "noise" signal.
Figure 8:
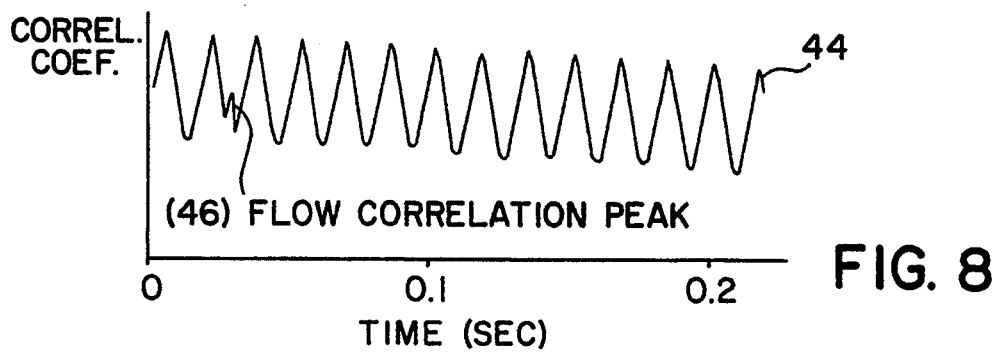
FIG. 8 is a graph of correlated data of FIG. 7.
Figure 9:
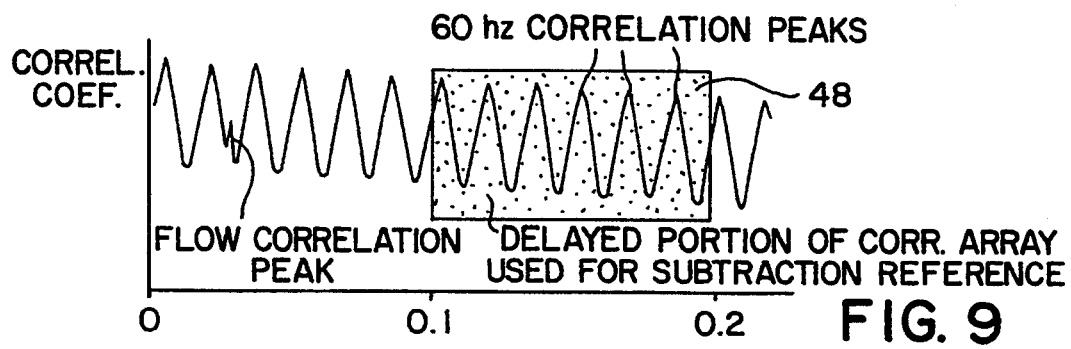
FIG. 9 is the graph of FIG. 8 showing a shaded portion from 0.1 to 0.2 seconds (six cycles)
Figure 10:
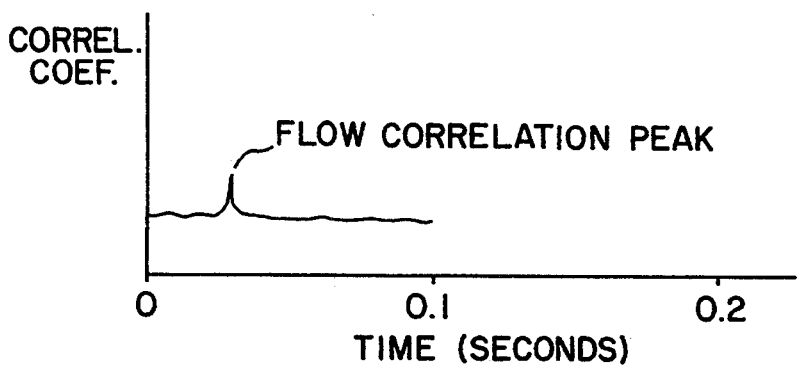
FIG. 10 shows the result of subtracting the shaded portion of FIG. 9 from the begining of the data of FIG. 9 whereby the noise signal is eliminated.

As in many sensitive systems, 60 cycle and 120 cycle noise from the power lines must be reduced. In countries having 50 Hz power systems, such noise is 50 and 100 Hz based. FIG. 7 shows a graph of raw data generated from the up and down stream sensors with a dominating continuous 60 Hz periodic signal 40. The flow signals of interest are found as minor peaks 42 riding on the larger periodic signal. Calculated cross correlation arrays will contain correlated peaks that occur at the same frequency as the periodic signal in the raw data. Cross correlating the raw signal of FIG. 7 results in a plot of correlation corefficients as shown in FIG. 8. The correlated signals (delayed in time) contain the relatively large 60 Hz component along with the smaller correlated flow signal 46. Such 60 Hz (or 50 Hz, etc.) power line noise is reduced by manipulating the data. The manipulation comprises subtracting a reference portion of the correlated array data (where the flow correlation peak does not occur) from the correlated array data where the flow correlation peak does occur. For this technique to be effective, the phase angle of the power line noise in the referenced correlated data array portion must be the same as that in the correlated data array portion containing the flow peak. In order to accomplish this, the referenced correlated array data is selected at some multiple of 0.1 seconds, since 0.1 seconds contains exactly 5 cycles of 50 Hz and 6 cycles of 60 Hz (and 10 and 12 cycles of 100 and 120 Hz, respectively). Thus the effects of the 50 or 60 Hz signal are removed by this subtraction. FIG. 9 shows a graph of the correlated array data with a shaded portion 48 which is subtracted from the beginning portion of the same graph. The result is shown in FIG. 10 where the larger 60 Hz signal is removed leaving only the flow correlation peak. The reference portion can be selected to ensure that the flow peak does not occur in the reference portion by knowing the flow rate used in a specific system. For example, with a known flow rate, the delay time, between the introduction of a solid catalyst in a flowing liquid hydrocarbon carrier and the flow peak "pulse" being sensed, is estimated. Consider the delay time to be in the ten to fifteen millisecond range (which is typical). With such a delay time, a reference portion is selected as the 0.1 second region between 0.1 and 0.2 seconds—an order of magnitude beyond the time that the flow peak signal will occur. This will ensure that the reference portion does not contain the flow peak. Similar selections, with different times, can be made in other applications of this technique.

The sensors are provided with intrinsically safe connections by techniques well known in the art. Such techniques (not shown) may be of the form of voltage clippers, MOV's and the like, resistances and combinations thereof where the energy of any possible discharge is limited so as to prevent an explosion. Physical areas that may be touched are current limited to human-safe levels. Also, the invention is implemented for safety in another preferred embodiment by providing double insulation.

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

What is claimed is:

1. In a chemical reaction process wherein selected flows of a material in a fluid carrier are fed to the reaction in metered amounts, an improved apparatus for on-line mass flow rate measuring, in a flowing two-component slurry mixture of the material in the liquid carrier, where the component being measured occupies a volume fraction and is of known specific gravity, said mixture flowing in a conduit of known cross section area and where the conduit has capacitive electrodes adjacent to the flow stream and triboelectric velocity probes spaced along the flow stream, comprising:

(a) means for measuring the capacitance between electrodes, said electrodes dispersed circumferentially around the flow such that the electric field lines between said electrodes, when charged, are about normal to the flow direction and the electric field lines penetrate the flow and the electrodes being of spiral form with a pitch and a length such that irregular distributions of the electric field are compensated, (b) means for relating the value of measured capacitances to the volume fraction of each component in the mixture, and (c) means for measuring the flow velocity by correlating the signals from the triboelectric probes, and (d) means for automatically computing the mass flow of the component being measured by multiplying together: the volume fraction, the velocity, the specific gravity of the material of the component being measured, and the cross section area.

2. Apparatus for measuring mass flow of at least one component in an on-line, two component slurry mixture of materials, where one component occupies a volume fraction and is of known specific gravity, where the dielectric constants of said materials are known, said slurry flowing in a conduit of known cross section area and where the conduit has capacitive electrodes adjacent to the flow stream and triboelectric probes spaced along the flow stream, comprising:

(a) means for sequentially measuring the capacitance between a plurality of said electrodes, said electrodes dispersed circumferentially around the flow such that the electric field lines in such capacitances, when charged, are about normal to the flow direction and the field lines penetrate the flow, (b), and the electrodes being of spiral form with a pitch and a length such that irregular distributions of the electric field are compensated, (c) means for relating the value of measured capacitances to the dielectric constants of the flowing materials, and (d) means for calculating the volume fraction from the dielectric constant of each component material and the known relationship of the dielectric constant of the entire flow to the dielectric constants of each component, (e) means for measuring the flow velocity by correlating the signals from the triboelectric probes, (f) means for computing the mass flow by multiplying the following together: the volume fraction, the velocity, the specific gravity of the fraction material, and the cross section area.

3. Apparatus as defined in claim 2 wherein the means for measuring flow velocity comprises:
an upstream velocity sensor;
a downstream velocity sensor, both velocity sensors at a known separation distance from each other,
means for receiving a signal at each velocity sensor, each of said received signals occurring due to charges in said flow moving past the velocity sensors, and
means for successively cross correlating the two signals at the velocity sensors with increasing time shifts until the cross correlation yields a maximum, and
means for calculating the flow velocity by dividing the separation distance by the time shift that produced the cross correlation maximum.

4. Apparatus as defined in claim 3 further comprising:
means for selecting a portion of the cross correlated received signal where no flow peak occurs,
means for subtracting said portion from the cross correlated received signal where the flow peak occurs, said subtraction is performed such that the power line signal contribution to the resulting cross correlated signal is removed.

5. Apparatus as defined in claim 3 wherein said electrodes are insulated from said flowing mixture materials.

6. Apparatus as defined in claim 2 further comprising:
means for measuring temperatures changes of the slurry mixture,
means for measuring the pressure changes in the slurry mixture, and
means for compensating for changes in dielectric constants of the materials responsive to temperature and pressure changes.

7. Apparatus as defined in claim 2 further comprising:
means for inputting a desired mass flow of at least one component,
means for determining the difference between the desired mass flow of said one component and the measured mass flow of said one component.
means for altering the mass flow of said one component, responsive to said difference, to reduce said difference, and
interactive means to input, store and display said desired mass flow, said measured mass flow, said specific gravity and dielectric constants of said mixture materials, said flow velocity and said volume fraction of a component.

* * * * *